US008203011B2

(12) United States Patent
Choi et al.

(10) Patent No.: US 8,203,011 B2
(45) Date of Patent: Jun. 19, 2012

(54) 3',4',5-TRIMETHOXY FLAVONE DERIVATIVES AS STIMULANT OF MUCUS SECRETION, METHOD FOR THE SAME, AND PHARMACEUTICAL COMPOSITION COMPRISING THE SAME

(75) Inventors: Seul-Min Choi, Suwon-si (KR); Kyung-Koo Kang, Suwon-si (KR); Dong-Sung Kim, Seoul (KR); Jeong-Hoon Kim, Yongin-si (KR); Byoung-Ok Ahn, Yongin-si (KR); Moo-Hi Yoo, Seoul (KR); Mi-Jeong Seo, Yongin-si (KR); Ju-Mi Kim, Yongin-si (KR); Yong-Duck Kim, Suwon-si (KR); Sun-Woo Jang, Seoul (KR); Yong-Sung Shon, Seoul (KR)

(73) Assignee: Dong-A Pharm. Co., Ltd., Seoul (KR)

( * ) Notice: Subject to any disclaimer, the term of this patent is extended or adjusted under 35 U.S.C. 154(b) by 238 days.

(21) Appl. No.: 12/451,902

(22) PCT Filed: Jun. 2, 2008

(86) PCT No.: PCT/KR2008/003078
§ 371 (c)(1),
(2), (4) Date: Dec. 4, 2009

(87) PCT Pub. No.: WO2008/150085
PCT Pub. Date: Dec. 11, 2008

(65) Prior Publication Data
US 2010/0130448 A1    May 27, 2010

(30) Foreign Application Priority Data
Jun. 7, 2007   (KR) .................. 10-2007-0055427

(51) Int. Cl.
*C07D 311/30*   (2006.01)
*A61K 31/352*   (2006.01)
(52) U.S. Cl. ....................... 549/403; 514/456
(58) Field of Classification Search .................. 549/403; 514/456
See application file for complete search history.

(56) References Cited

U.S. PATENT DOCUMENTS
6,025,387 A   2/2000   Yoo et al.

FOREIGN PATENT DOCUMENTS
| JP | 63-107971 A | 5/1988 |
| JP | 10-109982 A | 4/1998 |
| JP | 10-114766 A | 5/1998 |
| KR | 10-0447918 B1 | 4/1998 |
| KR | 10-0327621 B1 | 4/2001 |
| KR | 10-0644928 B1 | 11/2005 |
| WO | 2006/094357 A1 | 9/2006 |

OTHER PUBLICATIONS

Foulks, G.N. "What is dry eye and what does it mean to the contact lens wearer?". Eye & Contact Lens. 2003, vol. 29, No. 1S, pp. 96-100. Contact Lens Association of Ophthalmologists, Inc.
Jacobi, C., et al. "Das trockene Auge". Ophthalmologe. 2006. vol. 103, pp. 9-17. Springer Medizin Verlag.
Versura, P., et al. "Menopause and dry eye. A possible relationship". Gynecological Endocrinology. 2005, vol. 20, No. 5, pp. 289-298. ProQuest Pharma Collection.
Blehm, C., et al. "Computer vision syndrome: a review". Survey of Ophthalmology. 2005, vol. 50, No. 3, pp. 253-262. Elsevier Inc.
Oh, Han-Jin, et al. J Korean Ophthalmolog Soc. 2005, vol. 46, pp. 1774-1779.
Stevenson, D., et al. "Efficacy and safety of cyclosporin a ophthalmic emulsion in the treatment of moderate-to-severe dry eye disease". American Academy of Ophthalmology. 2000, vol. 107, pp. 967-974. Elsevier Science Inc.
Sall, K., et al. "Two multicenter, randomized studies of the efficacy and safety of cyclosporine ophthalmic emulsion in moderate to sever dry eye disease". American Academy of Ophthalmology. 2000, vol. 107, pp. 631-639.
Petrone, D., et al. "A double-blind, randomized, placebo-controlled study of cevimeline in Sjögren's syndrome patients with xerostomia and keratoconjunctivitis sicca". Arthritis & Rheumatism. 2002, vol. 46, No. 3, pp. 748-754.
Murakami, T., et al. "P2Y2 receptor stimulation increases tear fluid secretion in rabbits". Current Eye Research. 2000, vol. 21, No. 4, pp. 782-787. Swets & Zeitlinger.
Jumblatt, J.E., et al., "Regulation of Ocular mucin secretion by P2Y2 nucleotide receptors in rabbit and human conjunctiva". Exp. Eye Res. 1998, vol. 67, pp. 341-346. Academic Press.
Jumblatt, J.E., et al., "Characterization of human ocular mucin secretion mediated by 15(S)-HETE". Cornea. 2002, vol. 21, No. 8, pp. 818-824. Lippincott Williams & Wilkins, Inc., Philadelphia.
Urashima, H., et al., "Rebamipide increases the amount of mucin-like substances on the conjunctiva and cornea in the n-acetylcysteine-treated in vivo model". Cornea. 2004, vol. 23, No. 6, pp. 613-619. Lippincott Williams & Wilkins.
Drug Report: cyclosporine (ophthalmic, dry eye), Allergan. Thomson Pharma. 2010 Thomson Reuters. www.thomson-pharma.com.
Johnson, M.E., et al. "Changes in the tear film and ocular surface from dry eye syndrome". Progress in Retinal and Eye Research. 2004, vol. 23, pp. 449-474. Elsevier Ltd.
James E. Jumblatt, et al. "Characterization of Human Ocular Mucin Secretion Mediated by 15(S)-HETE," Cornea 21 (8): pp. 818-824, 2002.
T.E. Phillips, et al. "Lipoxygenase Metabolites of Arachidonic Acid do not Induce Mucus Secretion from Rabbit Intestinal Goblet Cells In Vitro," Prostaglandin Leukotrienes and Essential Fatty Acids (1989) 37, pp. 51-55.

*Primary Examiner* — Bernard Dentz
(74) *Attorney, Agent, or Firm* — Nath, Goldberg & Meyer; Mihsuhn Koh

(57) ABSTRACT

The present invention provides a 3',4',5-trimethoxy flavone derivative and a pharmaceutically acceptable salt thereof, preparation thereof, and a pharmaceutical composition for the treatment and prevention of dry eye syndrome comprising the same as an active ingredient.

The 3',4',5-trimethoxy flavone derivative and its pharmaceutically acceptable salt inhibit corneal damage through excellent stimulatory action on mucus secretion in the conjunctiva and therefore may be effective as a prophylactic or therapeutic agent for dry eye syndrome.

10 Claims, No Drawings

3',4',5-TRIMETHOXY FLAVONE DERIVATIVES AS STIMULANT OF MUCUS SECRETION, METHOD FOR THE SAME, AND PHARMACEUTICAL COMPOSITION COMPRISING THE SAME

This is a U.S. national phase Application filed under 35 U.S.C. 371 of PCT/KR2008/003078, filed 2 Jun., 2008 claiming priority benefit from KR Application No. 10-2007-0055427, filed 7 Jun. 2007, the entire content of which is hereby incorporated by reference.

TECHNICAL FIELD

The present invention relates to a 3',4',5-trimethoxy flavone derivative and a pharmaceutically acceptable salt thereof, preparation thereof, and a pharmaceutical composition for the treatment and prevention of dry eye syndrome comprising the same as an active ingredient.

BACKGROUND ART

Dry eye syndrome is a common clinical condition characterized by deficient tear production or excessive tear evaporation, which may be caused by a variety of causative factors. For example, lacrimal gland inflammation (dacryoadenitis) and corneal denervation may curb tear production, whereas meibomian gland dysfunction and eyelid disorders such as incomplete lid closure are frequently to blame for rapid tear evaporation. Further, T-cell-mediated inflammatory responses were reported responsible for the pathogenesis of dry eye syndrome (Eye Contact Lens, 29(1 Suppl):S96-100, 2003; and Opthalmologe, 103:9-17, 2006).

A tear film continuously secretes a given amount of tears which will not only provide sterilizing effects, but also participate in smooth covering and lubrication of ocular surfaces to play an important role in maintenance of one's eyesight. Three main layers make up the tear film. Specifically, the innermost layer is a layer of mucin produced by conjunctival goblet cells, the middle layer is an aqueous layer secreted by the lacrimal gland, and the most superficial layer is a very thin layer of lipids (fats or oils) secreted by the meibomian gland.

Usually, patients with dry eye syndrome may experience burning and stinging, grittiness or foreign-body sensation, itching, redness, and the other symptoms of ocular discomfort. In severe cases, vision may be substantially impaired. At first, dry eye syndrome was recognized as a characteristic sign of aging which is common among women of post-menopausal age. With recent increases in TV watching, use of computers, and wearing of contact lens, this condition becomes frequent in both men and women. Further, the onset age of dry eye syndrome is gradually decreasing (Gynecol Endocrinol, 20:289-98, 2005; and Surv Opthalmol, 50:253-62, 2005).

As approaches to remedy dry eye syndrome, mention may be made of instillation of artificial tears for artificial tear supplementation, instillation of steroidal anti-inflammatory eye drops to inhibit inflammatory responses, therapeutic contact lens (TCL) wear, surgical occlusion of the punctum to suppress tear escape from one's eye to result in prolonged ocular retention of artificial tear solutions or substitutes, and the like (J Korean Opthalmol Soc, 46:1774-1779, 2005). These therapeutic approaches have been widely used up to recently, but pose a variety of potential disadvantages and problems. For example, artificial tear preparations merely provide temporary and short-term effects, thus suffering from disadvantages such as the need for several daily applications of the tear preparations and no protective effects against corneal damage, whereas steroid preparations may cause the risk of irreversible side effects such as glaucoma, upon chronic administration of the steroid drug. In addition, therapeutic contact lens may provide inconvenience to users who are unfamiliar with wearing of contact lens, and may also be a potential source of bacterial infections. Further, the punctual occlusion surgery still suffers from disadvantages such as mental rejection feelings due to the surgical operation, and difficulty to restore the former state upon the occurrence of adverse side effects. However, the most glaring weakness of the aforementioned conventional remedies is in that they are merely symptomatic therapies, which are not focused to treat or address the root causes of dry eye conditions.

In 2006, the US company Allergan, Inc. developed and released Restasis (cyclosporine ophthalmic emulsion) which is a therapeutic agent for the treatment of dry eye syndrome using the immunomodulator cyclosporine. Restasis has recently been reported to inhibit the production and activation of immunocytes associated with the occurrence of keratoconjunctivitis sicca and to increase the tear secretion level (Opthalmology, 107:967-74, 2000; and Opthalmology, 107:631-9, 2000). Restasis exerts drug efficacy thereof via anti-inflammatory action, so long-term repeated drug administration of several months is unfortunately required to achieve therapeutic effects that are satisfactory to patients. Further, administration of Restasis is disadvantageously accompanied by relatively high frequency of occurrence (17%) of a typical side effect, e.g. burning sensation (Opthalmology, 107:631-9, 2000; and Thomson Pharma, www.thomson-pharma.com).

To this end, there is an urgent need for development of a therapeutic agent which is not a symptomatic therapeutic merely palliating symptoms of the concerned condition and is capable of treating the root causes of dry eye syndrome while securing safety of drug medications due to low manifestation of adverse side effects.

Dry eye syndrome is a multifactorial disease which is caused by diverse pathogenic causes as discussed hereinbefore, and a variety of approaches have been attempted to treat such a condition. Inter alia, a great deal of research has been actively focused on lacrimal secretion stimulants, i.e. tear stimulants. For example, attempts have been made to develop a drug that stimulates lacrimation (tear secretion) of lacrimal acinar cells through the medium of cholinergic neurotransmission or increases lacrimal flow of the conjunctiva via stimulation of purinergic receptors (Arthritis Rheum, 46:748-54, 2002; and Curr Eye Res, 21:782-7, 2000). In particular, an ocular mucin layer lowers the surface tension of water to allow uniform distribution of water throughout the ocular surface and plays an important role to provide corneal protection against a hostile external environment, such as ocular damage or infection by foreign materials or pathogenic agents. Therefore, many extensive animal-based preclinical and human-based clinical studies have been actively undertaken to find drugs that stimulate secretion of mucins from conjunctival goblet cells (Exp Eye Res, 67:341-6, 1998; Cornea, 21:818-24, 2002; Cornea, 23:613-9, 2004; and Thomson Pharma, www.thomson-pharma.com).

Mucus is composed mainly of mucin and inorganic salts. Mucin consists of carbohydrates and proteins and is responsible for protection of mucosal epithelial cells and lubricating action. To date, 21 different human mucin genes have been identified. Ocular mucin genes include 9 classes of genes, designated MUC1, MUC2, MUC4, MUC5AC, MUC7, MUC13, MUC15, MUC16 and MUC17, which may be further subdivided into transmembrane mucin and secretory mucin (Prog Retin Eye Res, 23:449-74, 2004). Substances having stimulatory activity on secretion of transmembrane and secretory mucins in tear films can be therapeutically effective for the treatment of dry eye syndrome by prevention of corneal damage which may arise from excessive eye dryness.

As a result of a variety of extensive and intensive studies and experiments to solve the problems as described above and to cope with the need for development of an effective therapeutic agent for the treatment of dry eye syndrome, the inventors of the present invention succeeded in synthesis of novel 3',4',5-trimethoxy flavone derivatives and pharmaceutically acceptable salts thereof and discovered that these compounds exhibit excellent effects on stimulation of conjunctival mucus secretion and inhibition of ocular surface damage. Further, the present inventors discovered that 7-carboxymethyloxy-3', 4',5-trimethoxy flavone monohydrates, previously studied in Korean Patent Nos. 447918, 327621 and 644928 assigned to the present applicant, have anti-inflammatory activity, gastric mucus secretion-stimulating activity and conjunctival mucus secretion-promoting activity, thereby providing pronounced inhibitory effects on the occurrence of ocular surface damage. The present invention has been completed based on these findings.

DISCLOSURE OF THE INVENTION

Technical Problem

It is an object of the present invention to provide a novel 3',4',5-trimethoxy flavone derivative or a pharmaceutically acceptable salt thereof.

It is another object of the present invention to provide a pharmaceutical composition for the treatment and prevention of dry eye syndrome, comprising a 3',4',5-trimethoxy flavone derivative or a pharmaceutically acceptable salt thereof as an active ingredient.

It is yet another object of the present invention to provide a pharmaceutical composition for the treatment and prevention of dry eye syndrome comprising 7-carboxymethyloxy-3',4', 5-trimethoxy flavone monohydrate as an active ingredient.

Technical Solution

In accordance with an aspect of the present invention, the above and other objects can be accomplished by the provision of a novel 3',4',5-trimethoxy flavone derivative represented by Formula 1:

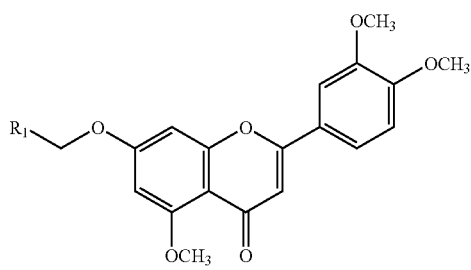

(1)

wherein $R_1$ is selected from the group consisting of tetrazolyl, carbamoyl, cyanocarbamoyl, N-benzenesulfonylcarbamoyl, hydrophosphoryl, hydroxyisopropylphosphoryl, aminosulfonylcarbamoyl, methylsulfonylcarbamoyl, carbamylcarbamoyl, formylcarbamoyl and acetylcarbamoyl; or a pharmaceutically acceptable salt thereof.

In accordance with another aspect of the present invention, there is provided a pharmaceutical composition for the treatment and prevention of dry eye syndrome comprising the aforesaid compound of Formula 1 as an active ingredient.

The compound of Formula 1 in accordance with the present invention may form a salt with a basic alkali metal such as $Na^+$, $K^+$, $Ca^{2+}$, $Mg^{2+}$, $Zn^{2+}$, or the like.

Hereinafter, the present invention will be described in more detail.

The present invention provides a novel 3',4',5-trimethoxy flavone derivative of Formula 1 or a pharmaceutically acceptable salt thereof.

Specifically, the present invention provides a compound selected from the group consisting of:

7-(tetrazol-5-ylmethyloxy)-3',4',5-trimethoxy flavone, 7-(tetrazol-5-ylmethyloxy)-3',4',5-trimethoxy flavone potassium salt, 7-{(carbamoyl)methyloxy}-3',4',5-trimethoxy flavone, 7-{(N-cyanocarbamoyl)-methyloxy}-3',4',5-trimethoxy flavone, 7-{(N-benzenesulfonylcarbamoyl)methyloxy}-3',4',5-trimethoxy flavone, 7-{(hydrophosphoryl)-methyloxy}-3',4',5-trimethoxy flavone, 7-{(hydroxyisopropylphosphoryl)-methyloxy}-3',4',5-trimethoxy flavone, 7-{(aminosulfonylcarbamoyl)methyloxy}-3',4',5-trimethoxy flavone, 7-{(methylsulfonylcarbamoyl)methyloxy}-3',4',5-trimethoxy flavone, 7-{(carbamylcarbamoyl)methyloxy}-3',4',5-trimethoxy flavone, 7-{(formylcarbamoyl)methyloxy}-3',4',5-trimethoxy flavone, and 7-{(acetylcarbamoyl)methyloxy}-3',4',5-trimethoxy flavone.

In the present invention, the compound of Formula 1 wherein $R_1$ is selected from the group consisting of carbamoyl, cyanocarbamoyl, N-benzenesulfonylcarbamoyl, aminosulfonylcarbamoyl, methylsulfonylcarbamoyl, carbamylcarbamoyl, formylcarbamoyl and acetylcarbamoyl (hereinafter, referred to as "compound of Formula 1-1'") may be prepared by condensation of a 7-carboxymethyloxy-3',4',5-trimethoxy flavone anhydride of Formula 2 with $R_2NH_2$ wherein $R_2$ is as defined below.

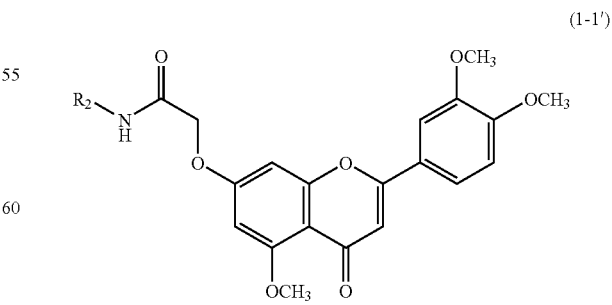

(1-1')

wherein $R_2$ is hydrogen, cyano, benzenesulfonyl, aminosulfonyl, methylsulfonyl, carbamyl, formyl or acetyl.

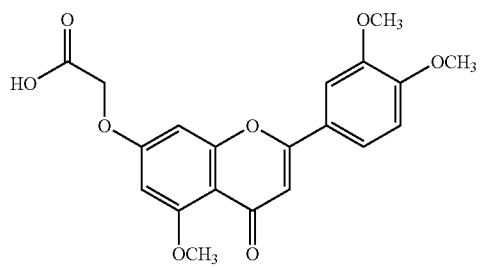

(2)

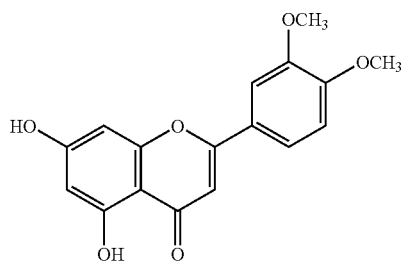

(3)

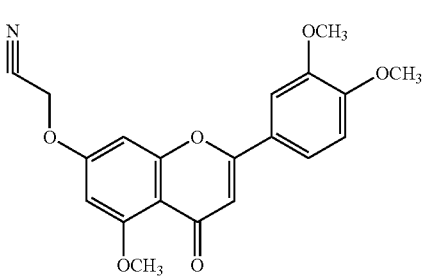

(4)

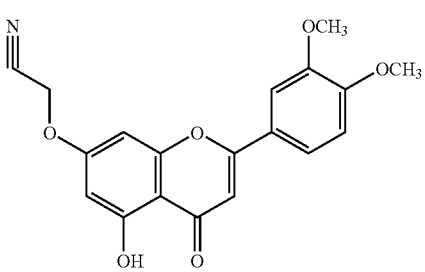

(5)

That is, the compound of Formula 1-1' in accordance with the present invention may be prepared by condensation of the 7-carboxymethyloxy-3',4',5-trimethoxy flavone anhydride of Formula 2 with $R_2NH_2$. The condensation may be carried out by dehydration with direct use of dicyclohexylcarbodiimide (DCC), diisopropylcarbodiimide (DIC) or 1-[3-(dimethylamino)propyl]-3-ethylcarbodiimide (EDC), or otherwise may be carried out by rendering a carboxyl group of the compound of Formula 2 into a highly reactive form such as an acid anhydride or an acid chloride, followed by reaction with $R_2NH_2$. The reaction temperature is preferably in a range of 0° C. to 100° C. The compound of Formula 1-1' may form a salt with a basic alkali metal, for example $Na^+$, $K^+$, $Ca^{2+}$, $Mg^{2+}$, $Zn^{2+}$, or the like.

Out of the compounds of Formula 1, the present invention further provides 7-(tetrazol-5-ylmethyloxy)-3',4',5-trimethoxy flavone of Formula 1-2' wherein $R_1$ is tetrazolyl and a pharmaceutically acceptable salt thereof.

The compound of Formula 1-2' is prepared by regioselective alkylation of the 7-hydroxy position in a 5,7-dihydroxy-3',4'-dimethoxy flavone of Formula 3 as a starting material to prepare a compound of Formula 4, methylation of the 5-hydroxy position in the compound of Formula 4 with a base and a methylating reagent in the presence of an aprotic solvent to prepare a compound of Formula 5, and cyclization of the compound of Formula 5 with sodium azide in the presence of an aprotic solvent such as dimethylformamide to thereby prepare a 7-(tetrazol-5-ylmethyloxy)-3',4',5-trimethoxy flavone of Formula 1-2'. The methylating reagent used to prepare the compound of Formula 5 may be methane iodide or dimethyl sulfate. The reaction temperature is preferably in a range of 0° C. to 150° C. Further, the base may be selected from the group consisting of potassium carbonate, sodium hydroxide, potassium hydroxide and sodium carbonate.

There is no particular limit to the aprotic solvent, so long as it is known to those skilled in the art. For example, mention may be made of 1,4-dioxane, tetrahydrofuran, ethyl acetate, ethyl ether, t-butylmethyl ether, N,N-dimethylformamide, N,N-dimethylacetamide, N-methylpiperidone, dichloromethane, 1,2-dichloroethane, acetonitrile, and the like.

The compound of Formula 1-2' may also form a salt with a basic alkali metal, for example $Na^+$, $K^+$, $Ca^{2+}$, $Mg^{2+}$, $Zn^{2+}$, or the like.

(1-2')

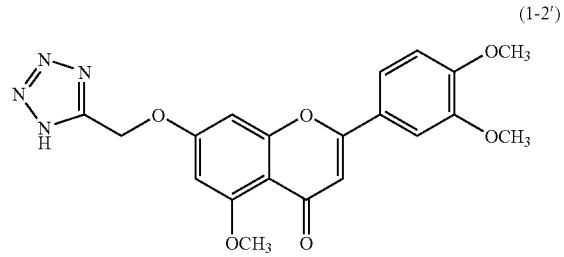

Further, the present invention provides a compound of Formula 1 wherein $R_1$ is hydrophosphoryl or hydroxyisopropylphosphoryl, and a pharmaceutically acceptable salt thereof.

Out of the compounds of Formula 1, a compound with $R_1$ being hydrophosphoryl or hydroxyisopropylphosphoryl (compound of Formula 1-3' or 1-3") is prepared by reacting a 7-hydroxy-3',4',5-trimethoxy flavone of Formula 6 with lower alkyl-protected phosphonyl halide $((R_{40})_2POCH_2X)$ to obtain a compound of Formula 7, and warming the compound of Formula 7 with sodium azide in the presence of an aprotic solvent or stirring the compound of Formula 7 under reflux in an acid aqueous solution to remove the $R_1$-protecting group.

As used herein, the term "acid aqueous solution" refers to an aqueous solution of strong acid. For example, mention may be made of a hydrochloric acid aqueous solution, a sulfuric acid aqueous solution, a phosphoric acid aqueous solution, and the like.

Removal of the $R_1$-protecting group is carried out by any deprotection scheme using $NaN_3$, hydrochloric acid and the like. Following such a process, a compound of Formula 1-3' or 1-3" in accordance with the present invention may be selectively obtained from the compound of Formula 7. Further, the compound of Formula 1-3' or 1-3" may form a salt following the reaction with a basic alkali metal such as $Na^+$, $K^+$, $Ca^{2+}$, $Mg^{2+}$, $Zn^{2+}$, or the like.

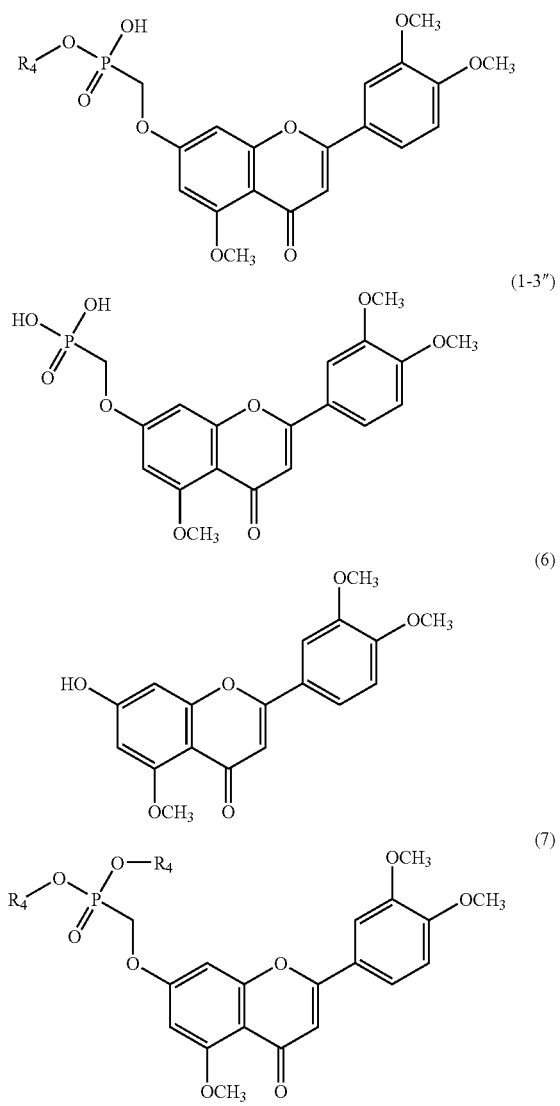

wherein $R_4$ is $C_1$-$C_6$ lower alkyl including methyl, ethyl and isopropyl.

In the phosphonyl halide (($R_{4O}$)$_2$POCH$_2$X), $R_4$ is as defined above, and X is chlorine, bromine or iodine.

Further, the present invention provides a pharmaceutical composition for the treatment and prevention of dry eye syndrome, comprising a 3',4',5-trimethoxy flavone derivative of Formula 1 or a pharmaceutically acceptable salt thereof as an active ingredient. Further, the present invention provides a pharmaceutical composition for the treatment and prevention of dry eye syndrome comprising a 7-carboxymethyloxy-3',4', 5-trimethoxy flavone monohydrate disclosed in Korean Patent No. 447918, 327621 or 644928, as an active ingredient.

Due to their excellent effects on stimulation of conjunctival mucus secretion and inhibition of ocular surface damage, the compounds of Formula 1 and 7-carboxymethyloxy-3',4',5-trimethoxy flavone monohydrates may be therapeutically and prophylactically effective for dry eye syndrome.

Further, the present invention provides a method for the treatment and prevention of dry eye syndrome, comprising administering to a mammal (including human) in need thereof a composition comprising a compound of Formula 1 or a pharmaceutically acceptable salt thereof or a 7-carboxymethyloxy-3',4',5-trimethoxy flavone monohydrate as an active ingredient.

Further, the present invention provides a use of a compound of Formula 1 or a pharmaceutically acceptable salt thereof or a 7-carboxymethyloxy-3',4',5-trimethoxy flavone monohydrate, for the preparation of a medicament for the treatment and prevention of dry eye syndrome.

Depending upon desired applications, the pharmaceutical composition of the present invention may be administered via a conventional route, for example by peroral administration or by parenteral administration (intradermally, subcutaneously, intravenously, intramuscularly, rectally, intranasally, and intraocularly). Further, the pharmaceutical composition may further comprise one or more conventional excipients taking into consideration desired dosage forms.

The compound of Formula 1 in accordance with the present invention may be administered at a dose of 0.001 to 1 mg/kg BW, once or several times a day, even though a higher or lower daily dose may be required for some patients. As will be apparent to those skilled in the art, the effective dose of the active compound may vary depending upon various factors such as co-administered drugs and severity of diseases.

Advantageous Effects

The present invention provides novel 3',4',5-trimethoxy flavone derivatives and pharmaceutically acceptable salts thereof. Due to having excellent stimulatory effects on mucus secretion in the conjunctiva and excellent inhibitory effects on ocular surface damage, the aforesaid 3',4',5-trimethoxy flavone derivatives can be therapeutically and prophylactically effective for dry eye syndrome.

MODE FOR INVENTION

Now, the present invention will be described in more detail with reference to the following Examples. These examples are provided only for illustrating the present invention and should not be construed as limiting the scope and spirit of the present invention.

Example 1

Preparation of 7-(tetrazol-5-ylmethyloxy)-3',4',5-trimethoxy flavone

Step 1: Preparation of 7-(cyanomethyloxy)-5-hydroxy-4',5'-dimethoxy flavones 5,7-dihydroxy-4',5'-dimethoxy flavone (20 g, 63.6 mmol, prepared according to the method disclosed in Korean Patent No. KR644928 assigned to the present applicant, Dong-A Pharm. Co., Ltd., Korea) and anhydrous potassium carbonate (20.3 g, 152.7 mmol) were dissolved in N,N'-dimethylformamide (400 mL) to which bromoacetonitrile (6 mL, 76.3 mmol) was then added dropwise at room temperature, followed by reaction for 13 hours. The reaction solution was inversely dispersed in a 1:4 mixed solution (1000 mL) of ethyl acetate and n-hexane and then stirred at room temperature for 1 hour. The resulting solids were filtered and dried under vacuum to quantitatively give 22.5 g of the title compound.

$^1$H NMR (400 MHz, DMSO-d$_6$): 12.98 (s, 1H), 7.71 (dd, 1H), 7.58 (d, 1H), 7.14 (d, 1H), 7.09 (s, 1H), 6.97 (d, 1H), 6.54 (d, 1H), 3.87 (s, 3H), and 3.84 (s, 3H)

Step 2: Preparation of 7-(cyanomethyloxy)-5,4',5'-dimethoxy flavones 7-(cyanomethyloxy)-5-hydroxy-4',5'-dimethoxy flavone (22.5 g) prepared in Step 1 and anhydrous potassium carbonate (51.7 g, 373.8 mmol) were added dropwise to 500 mL of acetone to which dimethyl sulfate (6.6 mL, 70 mmol) was then added dropwise, followed by stirring under reflux for 13 hours. The reaction solution was cooled to room temperature and chloroform (500 mL) was added dropwise thereto. Thereafter, the mixed solution was stirred for 30 min and filtered through celite. The celite pad was washed with chloroform (1000 mL) and the filtrate was evaporated to remove the solvent. The resulting solids were dissolved in chloroform (1000 mL) and washed with water. The organic layer was dried over anhydrous sodium sulfate and then evaporated to remove the solvent, and suspended with stirring in a 1:1 mixed solvent (1000 mL) of ethyl acetate and n-hexane for 2 hours. The resulting solids were dried under vacuum for 3 hours to give 6.47 g (yield: 28%) of the title compound.

$^1$H NMR (Varian 400 MHz, DMSO-$d_6$): 7.63 (dd, 1H), 7.52 (d, 1H), 7.11 (d, 1H), 7.03 (d, 1H), 6.82 (s, 1H), 6.63 (d, 1H), 5.34 (s, 2H), 3.87 (s, 3H), 3.85 (s, 3H), 3.84 (s, 3H), and 3.44 (brs, NH)

Step 3: Preparation of 7-(tetrazol-5-ylmethyloxy)-3',4',5-trimethoxy flavone 7-(cyanomethyloxy)-3',4',5-trimethoxy flavone (0.3 g, 0.82 mmol) obtained in Step 2, ammonium chloride (0.13 g, 2.45 mmol) and sodium azide (0.08 g, 1.23 mmol) were dissolved in N,N'-dimethylformamide (6 mL). After the reaction was carried out at 120° C. for 3 hours, the reaction solution was cooled to room temperature. The resulting solids were filtered and washed with ethyl acetate and n-hexane. The washed solids were dissolved in a 3:1 mixed solvent of chloroform and methanol and dried over anhydrous sodium sulfate to remove the solvent. The resulting residue was recrystallized from a 1:1 mixed solvent of ethyl acetate and chloroform to give 0.195 g (yield: 58%) of the title compound.

$^1$H NMR (Varian 400 MHz, DMSO-$d_6$): 7.61 (dd, 1H), 7.50 (d, 1H), 7.10 (d, 1H), 7.04 (d, 1H), 6.76 (s, 1H), 6.58 (d, 1H), 5.41 (s, 2H), 3.87 (s, 3H), 3.83 (s, 3H), and 3.81 (s, 3H)

Example 2

Preparation of 7-(tetrazol-5-ylmethyloxy)-3',4',5-trimethoxy flavone potassium salt 7-(tetrazol-5-ylmethyloxy)-3',4',5-trimethoxy flavone (0.13 g) prepared in Example 1 was dissolved in a 1N potassium hydroxide solution (5 mL). The solution was stirred at room temperature for 1 hour and the unreacted starting material was filtered. The resulting aqueous solution was lyophilized to afford 0.140 g (yield: 99%) of the title compound.

$^1$H NMR (Varian 400 MHz, DMSO-$d_6$): 7.62 (dd, 1H), 7.50 (d, 1H), 7.10 (d, 1H), 7.05 (d, 1H), 6.75 (s, 1H), 6.57 (d, 1H), 5.28 (s, 2H), 3.87 (s, 3H), 3.83 (s, 3H), 3.80 (s, 3H), and 3.35 (br)

Example 3

Preparation of 7-{(carbamoyl)methyloxy}-3',4',5-trimethoxy flavone 7-carboxymethyloxy-3',4',5-trimethoxy flavone anhydride (1 g, 2.59 mmol, prepared according to the method disclosed in Korean Patent No. KR447918 assigned to the present applicant, Dong-A Pharm. Co., Ltd., Korea) was dissolved in N,N'-dimethylformamide (20 mL) to which pyridine (130 μl), di-t-butyl dicarbonate (0.73 g, 3.34 mmol) and ammonium carbonate (0.27 g, 3.34 mmol) were then added dropwise. The solution was stirred at room temperature for 4 hours and then washed several times with ethyl acetate. The organic layer was dried over anhydrous magnesium sulfate, distilled under reduced pressure to remove the solvent, suspended with stirring in acetone for 2 hours, and filtered. The filtered solids were dried under vacuum to afford 0.44 g (yield: 44%) of the title compound.

$^1$H NMR (Varian 400 MHz, DMSO-$d_6$): 7.62 (d, 1H), 7.42 (d, 1H), 7.10 (d, 1H), 6.83 (d, 1H), 6.77 (s, 1H), 6.60 (d, 1H), 4.59 (s, 1H), 3.87 (s, 3H), 3.83 (s, 3H), 3.82 (s, 3H), and 3.31 (s, 2H)

Example 4

Preparation of 7-{(N-cyanocarbamoyl)-methyloxy}-3',4',5-trimethoxy flavone 7-carboxymethyloxy-3',4',5-trimethoxy flavone anhydride (1 g, 2.59 mmol, prepared according to the method disclosed in Korean Patent No. KR447918 assigned to the present applicant, Dong-A Pharm. Co., Ltd., Korea), N-3-dimethylaminopropyl-N'-ethylcarbodiimide hydrochloride (0.55 g, 2.87 mmol, Aldrich), dimethylaminopyridine (0.35 g, 2.87 mmol) and cyanamide (0.12 g, 2.87 mmol) were added dropwise at 0° C. and then reacted at room temperature for 4 hours. 20 mL of water was added dropwise to separate the organic layer from the aqueous layer and the aqueous layer was distilled off under reduced pressure. The resulting residue was purified by column chromatography using a 20:1 mixed solvent of dichloromethane and methanol as an eluent, thereby affording 0.33 g (yield: 31%) of the title compound.

$^1$H NMR (400 MHz, DMSO-$d_6$): 7.55 (dd, 1H), 7.46 (s, 1H), 7.04 (d, 1H), 6.69 (s, 1H), 6.59 (d, 1H), 6.38 (d, 1H), 4.36 (s, 2H), 3.86 (s, 3H), 3.81 (s, 3H), 3.76 (s, 3H), and 3.31 (s, 2H)

Example 5

Preparation of 7-{(N-benzenesulfonylcarbamoyl)methyloxy}-3',4',5-trimethoxy flavone 7-carboxymethyloxy-3',4',5-trimethoxy flavone anhydride (5 g, 12.9 mmol, prepared according to the method disclosed in Korean Patent No. KR447918 assigned to the present applicant, Dong-A Pharm. Co., Ltd., Korea), 1-3-dimethylaminopropyl-3-ethylcarbodiimide hydrochloride (2.48 g, 12.9 mmol, Aldrich) and 4-dimethylaminopyridine (2.37 mg, 19.4 mmol) were added to 150 mL of dichloromethane and stirred at room temperature for 20 min. Benzenesulfonamide (4.07 g, 25.88 mmol) was then added dropwise thereto, followed by reaction at room temperature for 13 hours. 20 mL of water was added dropwise to separate the organic layer from the aqueous layer and the aqueous layer was distilled off under reduced pressure. The resulting residue was purified by column chromatography using a 30:1 mixed solvent of dichloromethane and methanol as an eluent, thereby affording 1.02 g (yield: 15%) of the title compound.

$^1$H NMR (Varian 400 MHz, DMSO-$d_6$): 7.55 (dd, 1H), 7.46 (s, 1H), 7.04 (d, 1H), 6.69 (s, 1H), 6.59 (d, 1H), 6.38 (d, 1H), 4.36 (s, 2H), 3.86 (s, 3H), 3.81 (s, 3H), 3.76 (s, 3H), and 3.31 (s, 2H)

Example 6

Preparation of 7-{(hydrophosphoryl)-methyloxy}-3', 4',5-trimethoxy flavone

Step 1: Preparation of 7-{(diisopropylphosphoryl)-methyloxy}-3',4',5-trimethoxy flavone 7-hydroxy-3',4',5-trimethoxy flavone (3 g, 9.14 mmol, prepared according to the method disclosed in Korean Patent No. KR447918 assigned to the present applicant, Dong-A Pharm. Co., Ltd., Korea) was dissolved in dimethylformamide (50 mL) to which potassium carbonate (2.5 g, 2 eq.) and diisopropyl bromomethylphosphonate (3.5 g, 1.5 eq.) were then added. After the reaction was carried out at 90° C. for 16 hours, the reaction solution was cooled to room temperature and extracted two times with ethyl acetate. The organic layer was dried over magnesium sulfate and the solvent was distilled off under reduced pressure. The resulting residue was purified by silica gel column chromatography using a 1:4 mixed solvent of ethyl acetate and n-hexane as an eluent, thereby affording 1.46 g (yield: 32%) of the title compound.

$^1$H NMR (400 MHz, DMSO-$d_6$): 7.52 (d, 1H), 7.32 (dd, 1H), 6.95 (d, 1H), 6.65 (s, 1H), 6.48 (d, 1H), 4.86 (m, 2H), 4.31 (d, 2H), 3.97 (s, 3H), 3.96 (s, 3H), 3.95 (s, 3H), 1.40 (s, 3H), 1.39 (s, 6H), and 1.37 (s, 3H)

Step 2: Preparation of 7-{(hydrophosphoryl)-methyloxy}-3',4',5-trimethoxy flavone 7-{(diisopropylphosphoryl)-methyloxy}-3',4',5-trimethoxy flavone (0.6 g, 1.18 mmol) obtained in Step 1 was added dropwise to water (15 mL) and conc. hydrochloric acid (15 mL), followed by stirring under reflux for 2 hours. The reaction solution was cooled to room temperature. The resulting solids were filtered under reduced pressure, washed with water and acetone, and then dried to afford 0.21 g (yield: 42%) of the title compound.

$^1$H NMR (Varian 400 MHz, DMSO-$d_6$): 7.63 (dd, 1H), 7.52 (d, 1H), 7.09 (d, 1H), 6.97 (d, 1H), 6.77 (s, 1H), 6.51 (d, 1H), 4.26 (d, 2H), 3.87 (s, 3H), and 3.83 (s, 6H)

Example 7

Preparation of 7-{(hydroxyisopropylphosphoryl)-methyloxy}-3',4',5-trimethoxy flavone 7-{(diisopropylphosphoryl)-methyloxy}-3',4',5-trimethoxyflavone (0.5 g, 0.99 mmol, produced in Step 1 of Example 6) and sodium azide (0.5 g, 7.69 mmol) were added dropwise to N,N-dimethylformamide (20 mL) and warmed at 100° C. for 8 hours. The reaction solution was cooled to room temperature, and 50 mL of ethyl acetate and 50 mL of water were added dropwise, followed by separation of the organic layer from the aqueous layer. 10 mL of conc. hydrochloric acid was added dropwise to the aqueous layer which was then extracted with chloroform. The organic layer was washed with saturated saline, dried over anhydrous sodium sulfate and then evaporated to afford 0.15 g (yield: 33%) of the title compound.

$^1$H NMR (Varian 400 MHz, DMSO-$d_6$): 7.61 (dd, 1H), 7.50 (d, 1H), 7.08 (d, 1H), 6.97 (d, 1H), 6.76 (s, 1H), 6.52 (d, 1H), 4.62 (m, 1H), 4.36 (d, 1H), 3.88 (s, 3H), 3.87 (s, 3H), 3.85 (s, 3H), and 1.25 (d, 6H)

Example 8

Preparation of 7-{(aminosulfonylcarbamoyl)methyloxy}-3',4',5-trimethoxy flavone 7-carboxymethyloxy-3',4',5-trimethoxy flavone anhydride (1 g, 2.59 mmol, prepared according to the method disclosed in Korean Patent No. KR447918 assigned to the present applicant, Dong-A Pharm. Co., Ltd., Korea), sulfamide (0.27 g, 2.85 mmol) and diisopropylethylamine (0.9 mL, 5.18 mmol) were added to 10 mL of dichloromethane and then stirred at room temperature for 20 min. The reaction solution was cooled to −20° C. and benzotriazol-1-yl-oxy-tris-pyrrolidino-phosphonium hexafluorophosphate (1.48 g, 2.85 mmol, Aldrich) was added dropwise thereto, followed by reaction at room temperature for 8 hours. After the reaction was complete, the resulting solids were filtered and distilled under reduced pressure to remove the solvent. The residue was purified by column chromatography using a 20:1 mixed solvent of dichloromethane and methanol as an eluent, thereby affording 0.16 g (yield: 13%) of the title compound.

$^1$H NMR (Varian 400 MHz, DMSO-$d_6$): 13.16 (s, 1H), 7.63 (dd, 1H), 7.59 (d, 1H), 6.84 (d, 1H), 6.76 (s, 1H), 6.52 (d, 1H), 4.85 (s, 2H), 3.86 (s, 3H), 3.83 (s, 3H), and 3.82 (s, 3H)

Example 9

Preparation of 7-{(methylsulfonylcarbamoyl)methyloxy}-3',4',5-trimethoxy flavone 7-carboxymethyloxy-3',4',5-trimethoxy flavone anhydride (10 g, 25.9 mmol, prepared according to the method disclosed in Korean Patent No. KR447918 assigned to the present applicant, Dong-A Pharm. Co., Ltd., Korea), 1-[3-(dimethylamino)propyl]-3-ethylcarbodiimide hydrochloride (4.96 g, 25.9 mmol, Aldrich) and 4-dimethylaminopyridine (4.74 mg, 38.8 mmol) were added to 300 mL of dichloromethane and then stirred at room temperature for 20 min. Methanesulfonamide (4.92 g, 51.76 mmol) was added dropwise thereto, followed by reaction at room temperature for 13 hours. After the reaction was complete, the resulting solids were filtered and distilled under reduced pressure to remove the solvent. The residue was purified by column chromatography using a 30:1 mixed solvent of dichloromethane and methanol as an eluent, thereby affording 2.15 g (yield: 18%) of the title compound.

$^1$H NMR (Varian 400 MHz, DMSO-$d_6$): 12.08 (s, NH), 7.62 (dd, 1H), 7.51 (d, 1H), 7.10 (d, 1H), 6.82 (d, 1H), 6.78 (s, 1H), 6.56 (d, 1H), 4.87 (s, 2H), 3.86 (s, 3H), 3.83 (s, 3H), 3.78 (s, 3H), and 3.29 (s, 3H)

Example 10

Preparation of 7-{(carbamylcarbamoyl)methyloxy}-3',4',5-trimethoxy flavone 7-carboxymethyloxy-3',4',5-trimethoxy flavone anhydride (1 g, 2.59 mmol, prepared according to the method disclosed in Korean Patent No. KR447918 assigned to the present applicant, Dong-A Pharm. Co., Ltd., Korea), 1-[3-(dimethylamino)propyl]-3-ethylcarbodiimide hydrochloride (0.50 g, 2.59 mmol, Aldrich) and 4-dimethylaminopyridine (0.47 mg, 3.88 mmol) were added to 300 mL of dichloromethane and then stirred at room temperature for 20 min. Urea (0.17 g, 2.83 mmol) was added dropwise thereto, followed by reaction at room temperature for 13 hours. After the reaction was complete, the resulting solids were filtered and distilled under reduced pressure to remove the solvent. The residue was purified by column chromatography using a 30:1 mixed solvent of dichloromethane and methanol as an eluent, thereby affording 0.17 g (yield: 15%) of the title compound.

$^1$H NMR (Varian 400 MHz, DMSO-$d_6$): 10.29 (s, NH), 7.62 (d, 1H), 7.51 (s, 1H), 7.09 (d, 1H), 6.82 (d, 1H), 6.78 (s, 1H), 6.57 (d, 1H), 4.90 (s, 2H), 3.86 (s, 3H), 3.83 (s, 3H), and 3.78 (s, 3H)

Example 11

Preparation of 7-{(formylcarbamoyl)methyloxy}-3', 4',5-trimethoxy flavone 7-carboxymethyloxy-3',4',5-trimethoxy flavone anhydride (1 g, 2.59 mmol, prepared according to the method disclosed in Korean Patent No. KR447918 assigned to the present applicant, Dong-A Pharm. Co., Ltd., Korea), 1-[3-(dimethylamino)propyl]-3-ethylcarbodiimide hydrochloride (0.50 g, 2.59 mmol, Aldrich) and 4-dimethylaminopyridine (0.47 mg, 3.88 mmol) were added to 300 mL of dichloromethane and then stirred at room temperature for 20 min. Formylamide (0.11 mL, 2.84 mmol) was added dropwise thereto, followed by reaction at room temperature for 14 hours. After the reaction was complete, the resulting solids were filtered and distilled under reduced pressure to remove the solvent. The residue was purified by column chromatography using a 30:1 mixed solvent of dichloromethane and methanol as an eluent, thereby affording 0.18 g (yield: 17%) of the title compound.

$^1$H NMR (Varian 400 MHz, DMSO-$d_6$): 8.23 (s, 1H), 8.0 (s, NH), 7.65 (dd, 1H), 7.52 (d, 1H), 7.11 (d, 1H), 7.02 (d, 1H), 6.80 (s, 1H), 6.61 (d, 1H), 5.26 (s, 2H), 3.87 (s, 3H), 3.85 (s, 3H), and 3.83 (s, 3H)

Example 12

Preparation of 7-{(acetylcarbamoyl)methyloxy}-3', 4',5-trimethoxy flavone 7-carboxymethyloxy-3',4',5-trimethoxy flavone anhydride (1 g, 2.59 mmol, prepared according to the method disclosed in Korean Patent No. KR447918 assigned to the present applicant, Dong-A Pharm. Co., Ltd., Korea), 1-[3-(dimethylamino)propyl]-3-ethylcarbodiimide hydrochloride (0.50 g, 2.59 mmol, Aldrich) and 4-dimethylaminopyridine (0.47 mg, 3.88 mmol) were added to 300 mL of dichloromethane and then stirred at room temperature for 20 min. Acetamide (0.17 g, 2.84 mmol) was added dropwise thereto, followed by reaction at room temperature for 13 hours. After the reaction was complete, the resulting solids were filtered and distilled under reduced pressure to remove the solvent. The residue was purified by column chromatography using a 30:1 mixed solvent of dichloromethane and methanol as an eluent, thereby affording 0.18 g (yield: 17%) of the title compound.

$^1$H NMR (Varian 400 MHz, DMSO-$d_6$): 8.23 (s, 1H), 8.0 (s, NH), 7.65 (dd, 1H), 7.52 (d, 1H), 7.11 (d, 1H), 7.02 (d, 1H), 6.80 (s, 1H), 6.61 (d, 1H), 5.26 (s, 2H), 3.87 (s, 3H), 3.85 (s, 3H), and 3.83 (s, 3H)

In order to investigate beneficial effects of 3',4',5-trimethoxy flavone derivatives obtained in the foregoing Examples and 7-carboxymethyloxy-3',4',5-trimethoxy flavone monohydrates on dry eye syndrome, the above compounds were studied on mucin-secreting effects in the human mucoepidermoid pulmonary carcinoma cell line, and on therapeutic effects in dry eye syndrome-induced rabbits.

Experimental Example 1

Effects of 3',4',5-trimethoxy flavone Derivatives on Mucin Secretion

In order to examine stimulatory effects of 3',4',5-trimethoxy flavone derivatives in accordance with the present invention on mucin secretion, the following in vitro experiments were carried out.

$2\times10^5$ cells/well of the human mucoepidermoid pulmonary carcinoma cell line NCI-H292 (ATCC, #CRL-1848) were seeded on a 96-well plate, and treated with 3',4',5-trimethoxy flavone derivatives at various concentrations of 0.16 to 100 μg/mL for 24 hours. Thereafter, secretion levels of representative transmembrane mucin MUC4 and secretory mucin MUC5AC were measured by enzyme-linked immunosorbent assay (ELISA). The results thus obtained are given in Table 1 below.

TABLE 1

Stimulatory effects of 3',4',5-trimethoxy flavone derivatives on mucin secretion (% increase in mucin secretion vs. non-treated control group)

| Compounds | Concentrations (μg/mL) | | | |
|---|---|---|---|---|
|  | 0.8 | 4 | 20 | 100 |
| Example 1 | 18.7 | 28.1 | 57.8 | 52.0 |
| Example 3 | 2.2 | 6.6 | 10.4 | 15.8 |
| Example 4 | — | — | 4.3 | 25.2 |
| Example 5 | 43.9 | 45.4 | 35.4 | 70.9 |
| Example 8 | 4.4 | 10.2 | 15.4 | 21.4 |
| Example 9 | 9.7 | 15.9 | 37.4 | 43.3 |
| Example 10 | — | 6.7 | 15.4 | 25.9 |
| Example 12 | 15.2 | 13.6 | 20.5 | 30.2 |
| 7-carboxymethyloxy-3',4',5-trimethoxy flavone monohydrate | 24.8 | 39.1 | 52.5 | 75.9 |

From the experimental results, it was confirmed that 3',4', 5-trimethoxy flavone derivatives have stimulatory effects on secretion of mucin. These results suggest that 3',4',5-trimethoxy flavone derivatives of the present invention promote secretion of transmembrane and secretory mucins and therefore can be effectively used for the treatment of dry eye syndrome.

Experimental Example 2

Therapeutic Effects of 3',4',5-trimethoxy flavone Derivatives in Rabbit Dry-Eye Syndrome Model Male New Zealand White (NZW) rabbits were randomly assigned into two groups, each consisting of 5 animals. In order to induce dry eye syndrome, N-acetylcysteine was first dissolved at a concentration of 20% in physiological saline. Then, the rabbit's lower eyelid was pulled slightly away from the globe to form a cup shape and the above-prepared N-acetylcysteine solution was instilled into the conjunctival sac six times every 2 hours, resulting in establishment of an animal model of dry eye syndrome. 3',4',5-trimethoxy flavone derivatives were dissolved at a concentration of 0.5% in a 0.1N sodium hydroxide solution which was then titrated to pH 7.0 to 8.0 with 10% acetic acid. From the following day after induction of dry eye syndrome, the titrated 3',4',5-trimethoxy flavone derivatives were repeatedly instilled into conjunctival sacs of animals at a dose frequency of 4 times/day (0.1 mL/each time) for seven consecutive days. On the next day following the induction of dry eye syndrome and upon completion of the experiment, the degree of ocular surface damage was evaluated to calculate a damage decrease rate (%) using Rose Bengal assay, and mucus secretion in the conjunctiva was quantitatively analyzed using Alcian blue assay. More specifically referring to Rose Bengal assay, 10 μl of a 1% Rose Bengal solution was dropped into the eyes of animals, and distribution and intensity of Rose Bengal staining were scored according to the method disclosed in Urashima et al., Cornea, 23:613-9, 2004. For Alcian blue assay, the rabbit's conjunctivae were excised, weighed, stained with a 0.1% Alcian blue solution for 2 hours and then washed with a 0.25 M sucrose solution. Following extraction with a 0.5 M magnesium chloride solution, the absorbance was measured at 605 nm. The results thus obtained are given in Table 2 below.

TABLE 2

Therapeutic effects of 3',4',5-trimethoxy flavone derivatives in rabbit model of dry eye syndrome

| Compounds | Rose Bengal Assay Damage decrease rate (%) | Alcian Blue Assay Absorbance/g tissue |
|---|---|---|
| Normal animal group | 0.0 ± 0.0 | 0.56 ± 0.18 |
| Vehicle control group | 49.3 ± 6.5 | 0.16 ± 0.05 |
| Example 4 | 83.8 ± 4.6* | 0.24 ± 0.19* |
| Example 5 | 70.1 ± 5.2* | 0.32 ± 0.09* |
| Example 9 | 76.8 ± 8.4* | 0.35 ± 0.13* |
| 7-carboxymethyloxy-3',4',5-trimethoxy flavone monohydrate | 88.5 ± 4.7* | 0.38 ± 0.08* |

Values were given as Mean ± S.D.
*Shown statistically significant as compared to vehicle control group (p < 0.05)

As can be seen from the results of Table 2, it was confirmed that the animal groups with administration of a 0.1 N sodium hydroxide solution after induction of dry eye syndrome by N-acetylcysteine exhibit decreased conjunctival mucus secretion resulting in occurrence of ocular damage, as compared to the normal animal group. However, after repeated instillation of 3',4',5-trimethoxy flavone derivatives for 7 days, the conjunctivae of the drug-administered groups exhibited a statistically significant increase in the amount of mucus secretion, as compared to the vehicle control group. Further, ocular damage was also significantly inhibited in the 3',4',5-trimethoxy flavone derivative-administered groups. These results represent that 3',4',5-trimethoxy flavone derivatives of the present invention can be effectively used as a therapeutic agent for the treatment of dry eye syndrome due to having stimulatory effects on mucus secretion in the conjunctivae.

Hereinafter, Preparation Example will be illustrated for a therapeutic agent of the present invention.

Formulation Example 1

Ophthalmic Pharmaceutical Preparation

| Preparation of an eye-drop (1%) | |
|---|---|
| 3',4',5-trimethoxy flavone of Formula 1 | 1 g |
| pH-adjusting agent (NaOH) | 0.11 g |
| pH-adjusting agent (HCl) | 0.0135 g |
| Preservative (Benzalkonium chloride) | 0.01 g |
| Thickening agent (PVA) | 1 g |
| Osmotic pressure-regulating agent (NaCl) | 0.83 g |
| Solubilizer (sterile purified water) | 100 mL |

The above-listed ingredients were mixed to prepare an eye-drop as desired.

INDUSTRIAL APPLICABILITY

As apparent from the above description, the present invention provides novel 3',4',5-trimethoxy flavone derivatives and pharmaceutically acceptable salts thereof. Due to having remarkable effects on stimulation of conjunctival mucus secretion and inhibition of ocular surface damage, 3',4',5-trimethoxy flavone derivatives are therapeutically and prophylactically effective for dry eye syndrome.

What is claimed is:

1. A 3',4',5-trimethoxy flavone derivative compound represented by Formula 1:

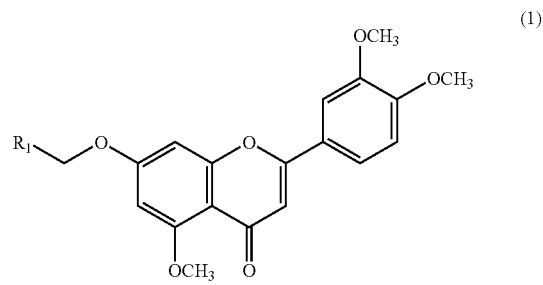

wherein $R_1$ is selected from the group consisting of tetrazolyl, carbamoyl, cyanocarbamoyl, N-benzenesulfonylcarbamoyl, hydrophosphoryl, hydroxyisopropylphosphoryl, aminosulfonylcarbamoyl, methylsulfonylcarbamoyl, carbamylcarbamoyl, formylcarbamoyl and acetylcarbamoyl;

or a pharmaceutically acceptable salt thereof.

2. The compound of claim 1, wherein the compound is selected from the group consisting of:

7-(tetrazol-5-ylmethyloxy)-3',4',5-trimethoxy flavone, 7-(tetrazol-5-ylmethyloxy)-3',4',5-trimethoxy flavone potassium salt, 7-{(carbamoyl)methyloxy}-3',4',5-trimethoxy flavone, 7-{(N-cyanocarbamoyl)-methyloxy}-3',4',5-trimethoxy flavone, 7-{(N-benzenesulfonylcarbamoyl)methyloxy}-3',4',5-trimethoxy flavone, 7-{(hydrophosphoryl)-methyloxy}-3',4',5-trimethoxy flavone, 7-{(hydroxyisopropylphosphoryl)-methyloxy}-3',4',5-trimethoxy flavone, 7-{(aminosulfonylcarbamoyl)methyloxy}-3',4',5-trimethoxy flavone, 7-{(methylsulfonylcarbamoyl)methyloxy}-3',4',5-trimethoxy flavone, 7-{(carbamylcarbamoyl)methyloxy}-3',4',5-trimethoxy flavone, 7-{(formylcarbamoyl)methyloxy}-3',4',5-trimethoxy flavone, and 7-{(acetylcarbamoyl)methyloxy}-3',4',5-trimethoxy flavone.

3. The compound of claim 1, wherein the pharmaceutically acceptable salt is a salt with a basic alkali metal selected from the group consisting of $Na^+$, $K^+$, $Ca^{2+}$, $Mg^{2+}$ and $Zn^{2+}$.

4. A process for preparing a compound represented by Formula 1-1':

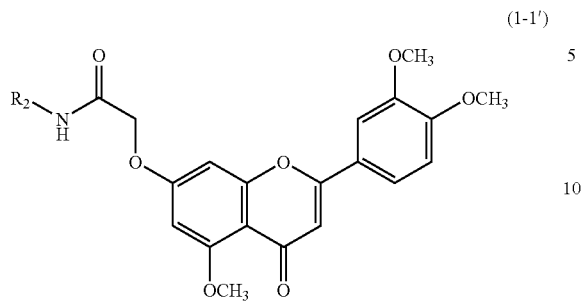
(1-1')

wherein $R_2$ is hydrogen, cyano, benzenesulfonyl, aminosulfonyl, methylsulfonyl, carbamyl, formyl or acetyl,
which comprises:
i) condensing a 7-carboxymethyloxy-3',4',5-trimethoxy flavone anhydride of Formula 2:

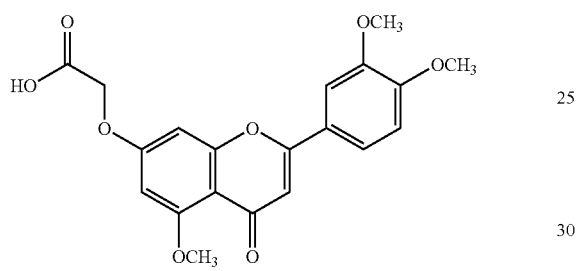
(2)

with $R_2NH_2$ ($R_2$ is as defined for Formula 1-1') to prepare a compound of Formula 1-1; and
   ii) optionally, reacting the compound of Formula 1-1' with an alkali metal to prepare a salt of the compound of Formula 1-1'.

5. A process for preparing a compound represented by Formula 1-2':

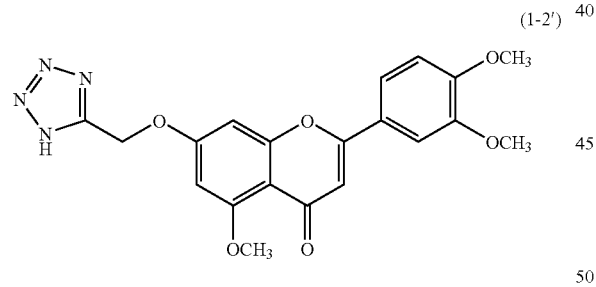
(1-2')

which comprises:
i) alkylating the 7-hydroxy position of a compound of Formula 3:

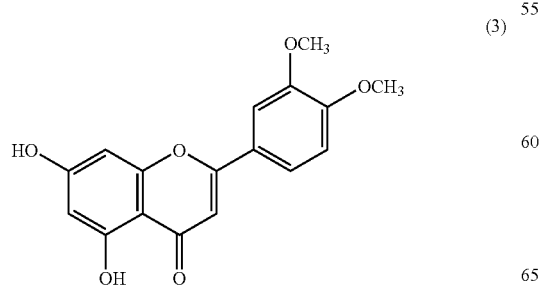
(3)

to prepare a compound of Formula 4:

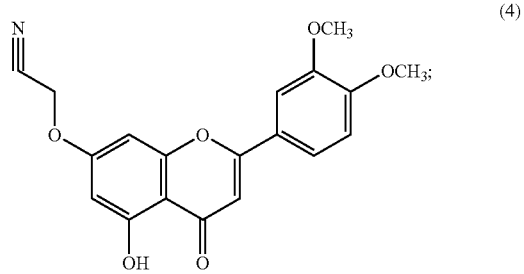
(4)

ii) methylating the 5-hydroxy position of the compound of Formula 4 with a base and a methylating reagent in the presence of an aprotic solvent to prepare a compound of Formula 5:

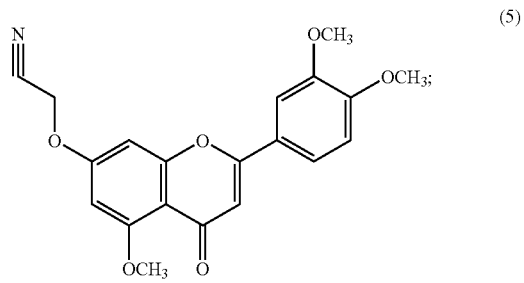
(5)

iii) cyclizing the compound of Formula 5 with sodium azide in the presence of an aprotic solvent to prepare a compound of Formula 1-2'; and
iv) optionally, reacting the compound of Formula 1-2' with an alkali metal to prepare a salt of the compound of Formula 1-2'.

6. A process for preparing a compound represented by Formula 1-3':

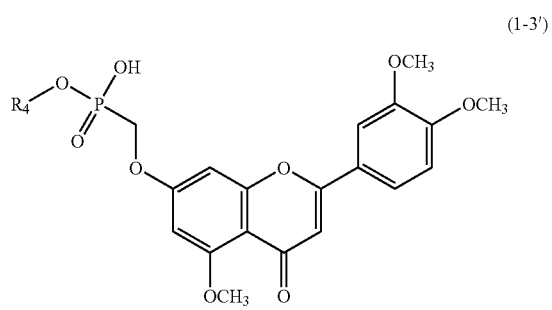
(1-3')

wherein $R_4$ is methyl, ethyl or isopropyl, or by Formula 1-3":

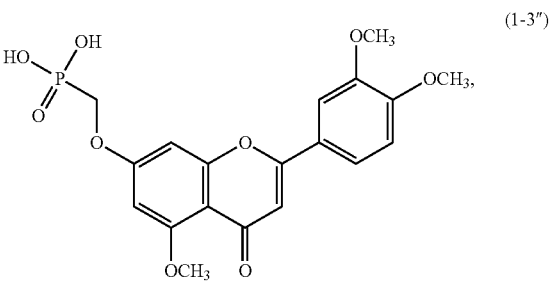
(1-3")

which comprises:
i) reacting a compound of Formula 6:

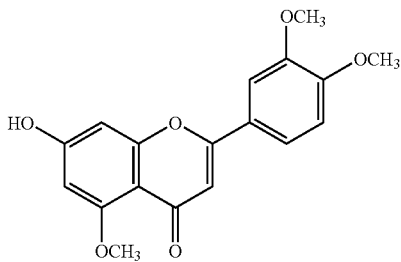

(6)

with phosphonyl halide (($R_{4O}$)$_2$POCH$_2$X: $R_4$ is as defined for Formula 1-3' and X is bromine, chlorine or iodine) to prepare a compound of Formula 7:

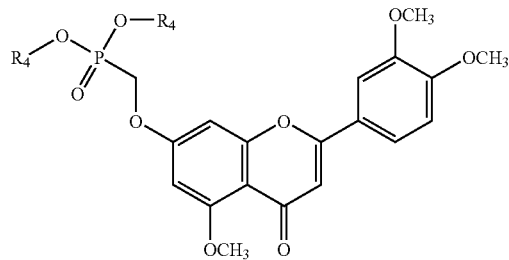

(7)

wherein each $R_4$ is as defined for Formula 1-3', and;
ii) warming the compound of Formula 7 with sodium azide in the presence of an aprotic solvent or stirring the compound of Formula 7 under reflux in an acid aqueous solution to prepare a compound of Formula 1-3' or 1-3"; and
iii) optionally, reacting the compound of Formula 1-3' or 1-3" with an alkali metal to prepare a salt of the compound of Formula 1-3' or 1-3".

7. A pharmaceutical composition for the treatment and prophylaxis of dry eye syndrome, comprising a compound of Formula 1 of claim 1 or a pharmaceutically acceptable salt thereof as an active ingredient.

8. A pharmaceutical composition for the treatment and prophylaxis of dry eye syndrome, comprising 7-carboxymethyloxy-3',4',5-trimethoxy flavone monohydrate as an active ingredient.

9. A method for the treatment and prophylaxis of dry eye syndrome, comprising administering to a mammal in need thereof a composition comprising a compound of Formula 1 of claim 1 or a pharmaceutically acceptable salt thereof as an active ingredient.

10. A method for the treatment and prophylaxis of dry eye syndrome, comprising administering to a mammal in need thereof a composition comprising 7-carboxymethyloxy-3',4',5-trimethoxy flavone monohydrate as an active ingredient.

* * * * *